(12) United States Patent
Kang et al.

(10) Patent No.: US 10,156,895 B2
(45) Date of Patent: Dec. 18, 2018

(54) PORTABLE HEALTHCARE DEVICE AND METHOD OF OPERATING THE SAME

(71) Applicant: SAMSUNG ELECTRONICS CO., LTD., Suwon-si (KR)

(72) Inventors: Jaemin Kang, Seoul (KR); Yongjoo Kwon, Yongin-si (KR); Sunkwon Kim, Suwon-si (KR); Younho Kim, Hwaseong-si (KR); Sangyun Park, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 133 days.

(21) Appl. No.: 14/797,692

(22) Filed: Jul. 13, 2015

(65) Prior Publication Data

US 2016/0162019 A1 Jun. 9, 2016

(30) Foreign Application Priority Data

Dec. 4, 2014 (KR) ........................ 10-2014-0173234

(51) Int. Cl.
| | |
|---|---|
| *G09G 5/00* | (2006.01) |
| *G06F 3/01* | (2006.01) |
| *G06F 19/00* | (2018.01) |
| *G06K 9/00* | (2006.01) |
| *H04N 9/31* | (2006.01) |
| *G06F 1/16* | (2006.01) |
| *G16H 40/63* | (2018.01) |

(52) U.S. Cl.
CPC .............. *G06F 3/011* (2013.01); *G06F 1/163* (2013.01); *G06F 1/1694* (2013.01); *G06F 3/015* (2013.01); *G06F 3/017* (2013.01); *G06F 19/00* (2013.01); *G06F 19/321* (2013.01); *G06K 9/00885* (2013.01); *G16H 40/63* (2018.01); *H04N 9/3173* (2013.01); *H04N 9/3179* (2013.01); *H04N 9/3194* (2013.01)

(58) Field of Classification Search
CPC .......... G06F 1/163; G06F 3/013; G06F 3/014; G06F 3/04883; G06F 3/0346; G06F 17/5009; G06F 19/321; G06F 3/012; G06F 3/147; G06F 1/1673; G06F 19/3468; G06F 1/1643; G06F 3/0416; G06F 2203/0331
USPC ........ 345/7–9, 156, 169, 172, 173, 175, 7–9
See application file for complete search history.

(56) References Cited

U.S. PATENT DOCUMENTS

| | | | |
|---|---|---|---|
| 8,379,488 B1 | 2/2013 | Gossweiler, III et al. | |
| 8,754,831 B2 * | 6/2014 | Kollin | G06F 1/1637 345/32 |
| 8,851,372 B2 * | 10/2014 | Zhou | G06F 1/163 235/380 |

(Continued)

FOREIGN PATENT DOCUMENTS

| | | |
|---|---|---|
| JP | 2006-259358 A | 9/2006 |
| JP | 2007-333929 A | 12/2007 |

(Continued)

*Primary Examiner* — Duc Q Dinh
(74) *Attorney, Agent, or Firm* — Sughrue Mion, PLLC

(57) ABSTRACT

A portable healthcare device and a method of operating the same are provided. The portable healthcare device detects biometric information of a user; obtains health state information of the user from the biometric information; and projects an image of the health state information, on a projection surface, in parallel with a reference axis, regardless of an orientation angle of the portable healthcare device.

13 Claims, 8 Drawing Sheets

(56) References Cited

U.S. PATENT DOCUMENTS

| | | | | |
|---|---|---|---|---|
| 2005/0276164 A1* | 12/2005 | Amron | | G04C 3/002 |
| | | | | 368/82 |
| 2009/0239579 A1* | 9/2009 | Lee | | G06F 1/1626 |
| | | | | 455/556.1 |
| 2010/0066763 A1* | 3/2010 | MacDougall | | G06F 1/1626 |
| | | | | 345/656 |
| 2012/0249409 A1* | 10/2012 | Toney | | G06F 3/017 |
| | | | | 345/156 |
| 2014/0055352 A1 | 2/2014 | Davis et al. | | |

FOREIGN PATENT DOCUMENTS

| | | |
|---|---|---|
| KR | 10-2009-0061179 A | 6/2009 |
| KR | 10-2014-0074824 A | 6/2014 |

* cited by examiner

PORTABLE HEALTHCARE DEVICE AND METHOD OF OPERATING THE SAME

CROSS-REFERENCE TO RELATED APPLICATION

This application claims priority from Korean Patent Application No. 10-2014-0173234, filed on Dec. 4, 2014 in the Korean Intellectual Property Office, the disclosure of which is incorporated herein in its entirety by reference.

BACKGROUND

1. Field

Apparatuses and methods consistent with exemplary embodiments relate to a portable healthcare device for displaying biometric information and a method of operating the same.

2. Description of the Related Art

As medical science advances and average life expectancy is prolonged, interest in health management and medical devices has increased. Such medical devices may include a small or medium-sized medical device used at public institutes, a small medical device or a healthcare device that may be owned or carried by a person, or various medical devices used at hospitals or health examination institutes.

SUMMARY

One or more exemplary embodiments provide methods and devices for displaying biometric information on a part of a user's body by using a portable healthcare device and a method of operating the same.

According to an aspect of an exemplary embodiment, there is provided a portable healthcare device including: a first sensor configured to detect biometric information of a user; a processor configured to obtain health state information of the user from the biometric information; a projector configured to be disposed on a first area of the user and project an image of the health state information on a projection surface that is a second area of the user; and a controller configured to control the projector to project the image of the health state information in parallel with a reference axis, regardless of an orientation angle of the portable healthcare device.

The portable healthcare device may further include an angle sensor configured to detect the orientation angle of the portable healthcare device that corresponds to an angle between the projection surface and the reference axis, wherein the controller determines an angle at which the image of the health state information is to be displayed based on the detected angle, and controls the projector to rotate the health state information through the determined angle and display the rotated image.

The determined angle may have a same absolute value as an absolute value of the detected angle and is in a reverse direction to the detected angle.

The reference axis may be an axis that connects a left side of the user to a right side of the user in a plane obtained by extending the projection surface.

The first area may be a wrist of the user.

The second area may be a hand of the user.

The portable healthcare device may further include a motion sensor configured to detect movement of the projection surface.

If the detected movement includes rotational movement of the projection surface, the controller may determine the angle at which the health state information is to be displayed in correspondence with the rotational movement.

The angle at which the health state information is to be displayed may have a same absolute value as an absolute value of a rotation angle of the rotational movement and be in a reverse direction to the rotation angle of the rotational movement.

If the detected movement includes linear movement of the projection surface, the controller may change content of the health state information in correspondence with the linear movement.

The controller may control the projector to display detailed information of the health state information in response to determining that the projection surface has moved toward the user's eyes due to the linear movement.

The controller may control the projector to display brief information of the health state information in response to determining that the projection surface has moved away from the user's eyes due to the linear movement.

The controller may control the projector to display the health state information, in response to determining that the projection surface is not moved based on a result of the detecting performed by the motion sensor.

According to an aspect of another exemplary embodiment, there is provided a method of operating a portable healthcare device including: detecting biometric information of a user; obtaining health state information of the user from the biometric information; projecting an image of the health state information on a projection surface of the user' body in parallel with a reference axis, regardless of an orientation angle of the portable healthcare device.

The method may further include: detecting an angle between the projection surface and the reference axis; determining the detected angle between the projection surface and the reference axis as the orientation angle; and determining an angle at which the health state information is to be displayed based on the detected angle, wherein the displaying the image of the health state information includes rotating the image of the health state information through the determined angle and displaying the rotated image on the projection surface.

The determined angle may have a same absolute value as an absolute value of the detected angle and be in a reverse direction to the orientation angle.

The reference axis may be an axis that connects a left side of the user to a right side of the user in a plane obtained by extending the projection surface.

The projection surface may be a hand of the user.

The portable healthcare device may further include detecting movement of the projection surface, wherein, if the detected movement includes linear movement of the projection surface, the displaying of the health state information includes changing and displaying content of the health state information in correspondence with the linear movement.

The changing and the displaying of the content of the health state information may include displaying detailed information of the health state information in response to determining that the projection surface has moved toward the user's eyes due to the linear movement, and displaying brief information of the health state information in response to determining that the projection surface has moved away from the user's eyes due to the linear movement.

BRIEF DESCRIPTION OF THE DRAWINGS

The above and/or other aspects will be more apparent by describing certain exemplary embodiments, with reference to the accompanying drawings, in which.

DETAILED DESCRIPTION

Figure 1:
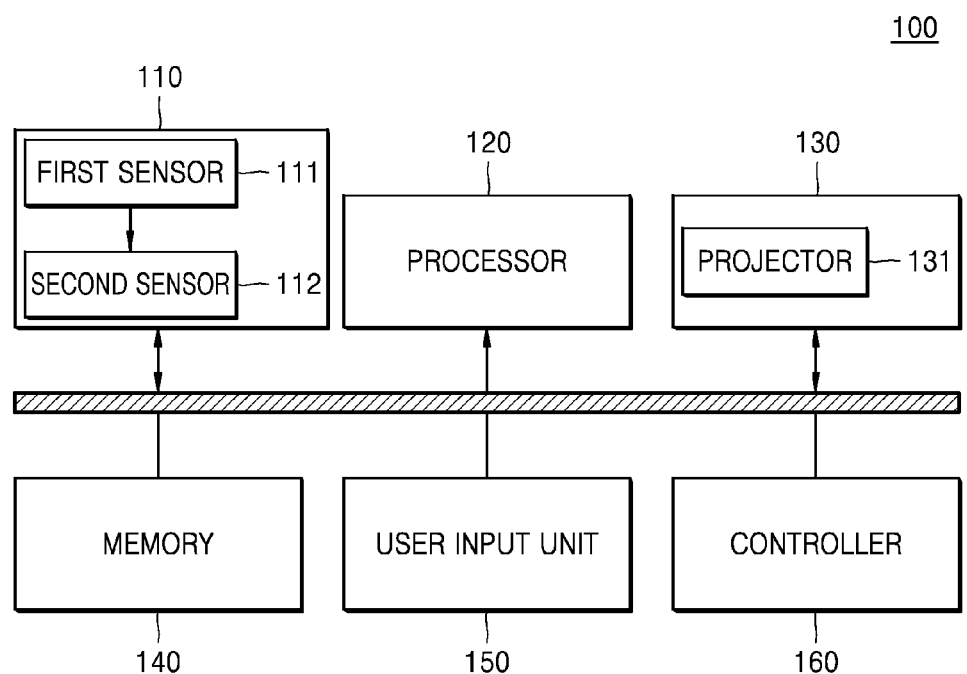
FIG. 1 illustrates a block diagram of a portable healthcare device according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "connected to" or "coupled to" another element, it may be "directly connected or coupled" to the other element, or "electrically connected to" the other element with intervening elements therebetween. It will be further understood that the terms "comprises," "comprising," "includes," and/or "including," when used herein, specify the presence of components, but do not preclude the presence or addition of one or more other components, unless otherwise specified. Additionally, terms used herein, such as 'unit' or 'module', mean entities for processing at least one function or operation. These entities may be implemented by hardware, software, or a combination of hardware and software.

It will be further understood that terms "comprises," "comprising," "includes," and/or "including," should not be interpreted as including all components or operations specified herein. It will be understood that some components or some operations may not be included, and additional components or operations may be further included.

According to an exemplary embodiment, a portable healthcare device 100 may be a device carried by a user, for example, a wearable device. The portable healthcare device 100 may be one selected from a wristwatch-type device, a bracelet-type device, a ring-type device, and a hair band-type device, or a combination thereof. According to exemplary embodiments, it is assumed that that the portable healthcare device 100 is a wristwatch-type device or a wrist band-type device. However, exemplary embodiments are not limited thereto.

FIG. 1 illustrates a block diagram of the portable healthcare device 100 according to an exemplary embodiment. As shown in FIG. 1, the portable healthcare device 100 may include a sensor 100 that may detect biometric information of a user, a processor 120 that may obtain health state information of the user by using the biometric information received from the sensor 110, an output unit 130 that may output the obtained health state information, a memory 140 that may store a program that may be used for the portable healthcare device 100, a user input unit 150 that may receive an input of a user command, and a controller 160 that may control elements of the portable healthcare device 100.

The user may be a subject whose biometric information is to be detected, and the biometric information may be used to administer health care to the user. Biometric information is a unique signal generated from the user. For example, biometric information may be a signal that is generated according to a motion of a particular part of the subject such as a heart or muscle, for example, electrocardiogram (ECG), ballistocardiogram (BCG), photoplethysmograph (PPG), electromyogram, electrocardiography, or a blood pressure, or may be information about substances included in the user, for example, blood sugar (for example, fasting plasma glucose or a glucose increase rate), cholesterol, or a bioelectrical impedance. The signal may be an optical signal or an ultrasound signal.

Health state information may be obtained by using biometric information. For example, health state information such as a highest blood pressure, a lowest blood pressure, or a blood vessel health index may be obtained by using biometric information such as ECG or PPG. Additionally, health state information such as body composition, for example, human body fat, skeletal muscle, a visceral fat amount, basal metabolism, a hydration level, triglyceride (TG), low-density lipoprotein (LDL), or low-density lipoprotein (HDL), a ratio between LDL and HDL, or a stress index may be obtained by biometric information about a bioelectrical impedance. Information about fasting plasma glucose or a glucose increase rate may be obtained by using biometric information about blood glucose.

The sensor 110 may include a first sensor 111 that may detect biometric information. The first sensor 111 may detect biometric information by using a non-invasive method. For example, the first sensor 111 may include a plurality of electrodes, and at least a part of the plurality of electrodes may contact the user when the user wears the portable healthcare device 100. Thus, the first sensor 111 may detect biometric information by detecting a change in electrical characteristics, for example, a change in the bioelectrical impedance according to a change in the biometric information. The first sensor 111 may detect biometric information by using light is emitted toward and reflected from the user. Here, the first sensor 111 may recognize the light as an optical signal. The first sensor 111 may also detect the biometrical information by using a magnetic signal or pressure.

The sensor 110 may include a second sensor 112 that may detect at least one of a location, a position, an orientation angle, a rotational angle, a direction, and movement of the portable healthcare device 100. The second sensor 112 may detect at least one of a location, a position, an orientation angle, a rotational angle, a direction, and movement of a projection surface with respect to the portable healthcare device 100 which will be described later. The second sensor 112 may include at least one of an angle sensor and a motion sensor. For example, the second sensor 112 may be an acceleration sensor, a gyro sensor, a terrestrial magnetic sensor.

The processor 120 may obtain health state information by using biometric information. The processor 120 may convert the health state information into an image or text. Additionally, the processor 120 may convert the health state information into an audible frequency. The processor 120 may be implemented in the form of a microprocessor module or in the form into which two or more microprocessors are combined. In other words, an implementation type of the processor 120 is not limited thereto.

The processor 120 may employ various methods of obtaining the health state information according to a type of biometric information. For example, if the biometric information is a bioelectrical impedance, the processor 120 may obtain body composition of the user by using the bioelectrical impedance. Additionally, the processor 120 may obtain bioelectrical composition with reference to user information, as well as the bioelectrical impedance. User information may be information about an age, a weight, a height, or a gender of the user.

Alternatively, if the biometric information is an ECG signal generated according to movement of a heart (i.e., heart contraction and relaxation), the processor 120 may obtain a waveform of a biometric information from the biometric information, and obtain health state information such as a highest blood pressure or a lowest blood pressure from the waveform of the biometric information. The processor 120 may amplify an ECG signal and filter the amplified ECG signal by using a finite impulse response (FIR) bandpass filter so as to obtain the waveform of the biometric information. Then, peaks are detected from the filtered ECG signal, and the waveform of the biometric information may be obtained by adaptively filtering the detected peaks.

The output unit 130 may output health state information. The output unit 130 may include a projector 131 that may display the health state information of the user to a part of the user's body. The projector 131 is a device that defines an area other than in the portable healthcare device 100 as a projection surface, and projects light toward the projection surface, so that the user may view the health state information.

Even though the portable healthcare device 100 includes a display that may display an image of the health state information, a size of the image of the health state information may be limited due to a size of a screen of the display. Accordingly, it may be desirable to increase the size of the screen of the display to enlarge the size of the image. However, this may worsen portability.

Accordingly, according to an exemplary embodiment, the portable healthcare device 100 may include the projector 131 that may define a part of the user's body as a projection surface, and displaying information on the projection surface. According to an exemplary embodiment, the portable healthcare device 100 may not include a display, but is not limited thereto. According to another exemplary embodiment, the output unit 130 included in the portable healthcare device 100 may further include the display, a sound output unit that may output the health state information as a sound signal having an audible frequency, or a light-emitter that may output the health state information as light.

The memory 140 may store data generated when the portable healthcare device 100 performs an operation. According to an exemplary embodiment, the memory 140 is a general storage medium, and may include a hard disk drive (HDD), a read-only memory (ROM), a random-access memory (RAM), a flash memory, and a memory card.

The user input unit 150 may receive an input for operating the portable healthcare device 100 from the user. The user input unit 150 may include a button, a key pad, a switch, a dial, a touch interface, or a voice recognition interface so that the user may directly operate the portable healthcare device 100.

The controller 160 may control all operations of the portable healthcare device 100. For example, the controller 160 may control the first sensor 111 to detect biometric information. Additionally, the controller 160 may determine whether the obtained health state information is normal or abnormal, and provide a result of the determining to the user via the output unit 130. The controller 160 may employ various methods of displaying the health state information by using a result of detecting performed by the second sensor 112. For example, the controller 160 may control the projector 131 to display the health state information to be in parallel with a reference axis. The method of displaying the health state information is described later.

Additionally, the portable healthcare device 100 may further a communication unit that may communicate with an external apparatus, and may have other various functions.

Figure 2:
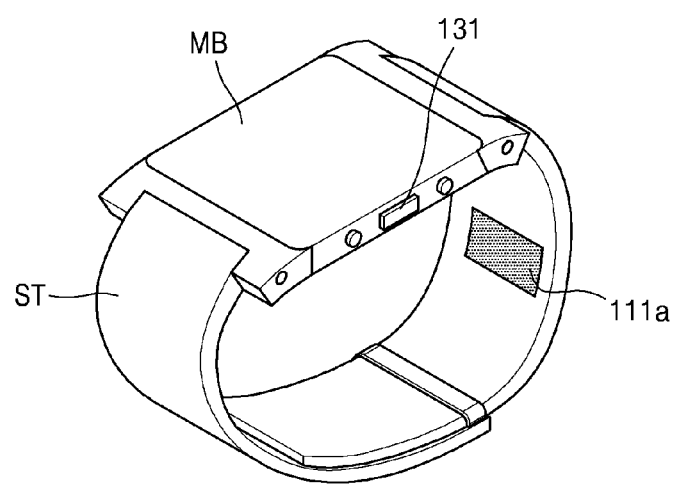
FIG. 2 illustrates a diagram showing an example of an appearance of the portable healthcare device according to an exemplary embodiment.

FIG. 2 illustrates a diagram showing an example of an appearance of the portable healthcare device 100 according to an exemplary embodiment.

The portable healthcare device 100 may include a main body MB and straps ST. Two straps ST are provided and are respectively connected to two sides of the main body MB so that the portable healthcare device 100 is worn on a part of the user's body, for example, a wrist. The processor 120, the output unit 130, the memory 140, the user input unit 150, and the controller 160 included in the portable healthcare device 100 may be disposed at the main body MB. The main body MB may further include a watch module so that the portable healthcare device 100 may be also used as a watch.

A component 111a of the first sensor 111 for detecting biometric information may be disposed at the strap ST or the main body MB. The component 111a of the first sensor 111 may be exposed to the outside of the strap ST so that the component 111 is able to be in contact with the user. For example, if the first sensor 111 detects a bioelectrical impedance, the first sensor 111 may include an electrode module that may apply current to the user and detect a voltage from the user. Alternatively, if the first sensor 111 includes an optical sensor that may detect biometric information by using light, the optical sensor may also be disposed at a location where the optical sensor may contact skin of the user.

The projector 131 included in the output unit 130 may be disposed at a side surface of the portable healthcare device 100, for example, at a side surface of the main body MB, so as to use skin of the user as a projection surface. Additionally, the second sensor 111 for detecting at least one of a location, a position, an orientation angle, a rotational angle, a direction, and movement of a projection surface may be disposed at the main body MB. For example, the second sensor 112 may be disposed at a projection axis that is to be described later.

Figure 3:
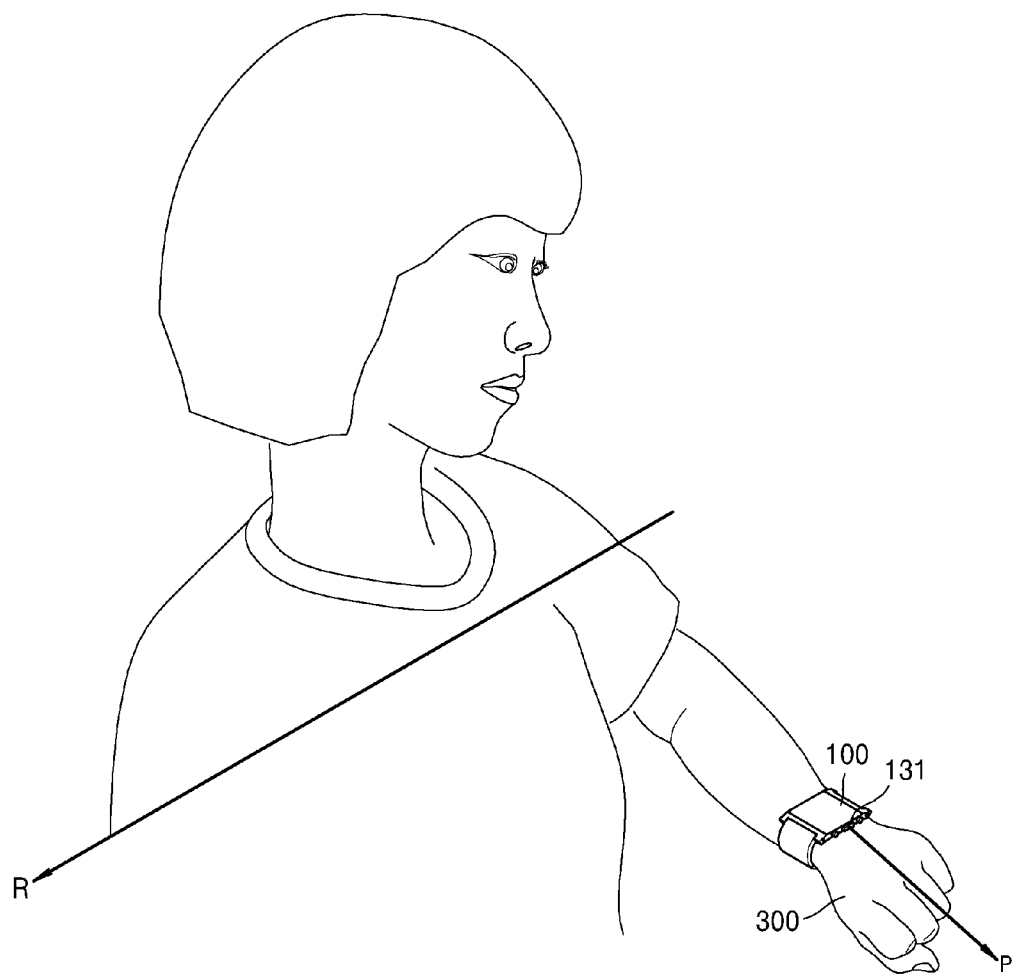
FIG. 3 illustrates a diagram showing an example of a state when a user wears the portable healthcare device, according to an exemplary embodiment.

FIG. 3 illustrates a diagram illustrating an example of a state when a user wears the portable healthcare device 100, according to an exemplary embodiment. As shown in FIG. 3, the user may wear the portable healthcare device 100 on his/her wrist. When the portable healthcare device 100 is worn, the first sensor 111 may contact skin of the user. For example, if the first sensor 111 includes a plurality of electrodes, some electrodes may contact skin of the user, and the other electrodes may be exposed to outside.

If the portable healthcare device 100 is worn by the user, an area of skin of the user, which is adjacent to another area on which the portable healthcare device 100 is worn (hereinafter, referred to as a 'wearing area'), may be a projection surface 310 of the projector 131. For example, if the portable healthcare device 100 is worn on a wrist of the user, a hand of the user may be the projection surface 310. The projection surface 310 may vary according to a wearing area. In FIG. 3, a back of the user's hand is shown as the projection surface 310. A center axis of the projection surface is referred to as a projection axis P. Since the portable healthcare device 100 is worn on the user's wrist, the projection axis P may be in parallel with an axis of the wrist.

An axis that connects a left side to a right side of the user, in a plane obtained by extending the projection surface 310, is referred to as a reference axis R. A location and movement of the projection surface 310 respectively correspond to a location and movement of the projection axis P. Thus, an angle between the projection axis P and the reference axis R and movement of the projection axis P respectively refer to an angle between the projection surface 310 and the reference axis R and movement of the projection surface 310.

According to an exemplary embodiment, the second sensor 112 included in the portable healthcare device 100 may be disposed at the projection axis P so as to detect at least one of a location and movement of the projection axis P. For example, the second sensor 112 may detect an angle between the projection axis P and the reference axis R, rotational movement of the projection axis P, or linear movement of the projection axis P. The second sensor 112 may be an angle sensor, a gyro sensor, or an acceleration sensor. Hereinafter, an angle between the projection surface 310 and the reference axis R and movement of the projection surface 310 are described as an angle between the projection axis P and the reference axis R and movement of the projection axis P.

Figure 4:
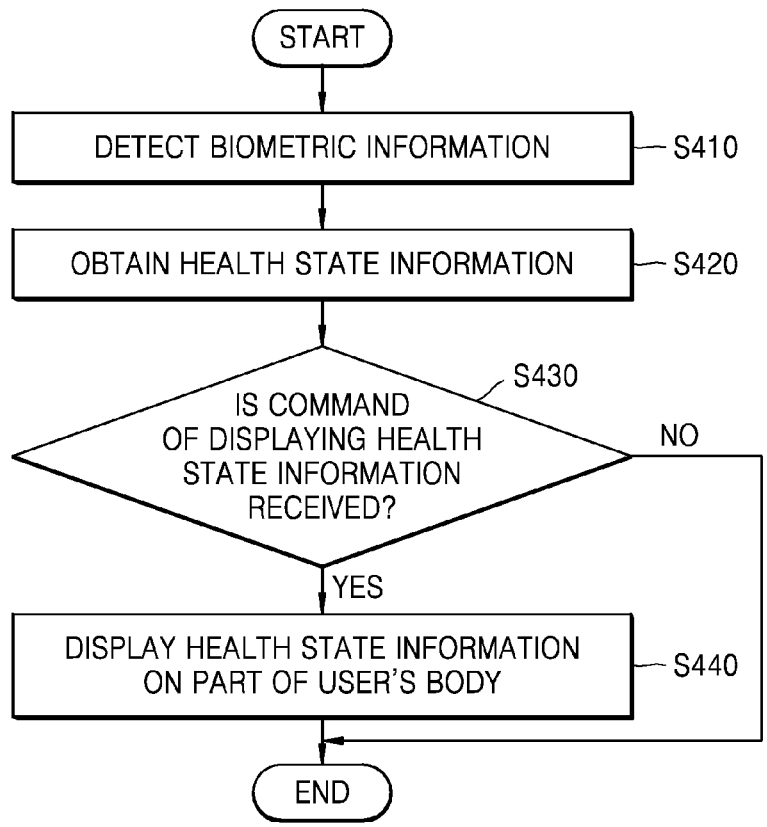
FIG. 4 illustrates a flowchart of a method of operating the portable healthcare device, according to an exemplary embodiment.

FIG. 4 illustrates a flowchart of a method of operating the portable healthcare device 100, according to an exemplary embodiment. Referring to FIG. 4, in operation S410, the first sensor 111 may detect biometric information. The biometric information is information related to health, and may be detected through skin of a user. The first sensor 111 may detect biometric information by using a non-invasive method. For example, the first sensor 111 may detect biometric information about a bioelectrical impedance, ECG, BCG, PPG, electromyogram, blood glucose, or cholesterol through skin of the user, by using a plurality of electrodes or light.

In operation S420, the processor 120 may obtain health state information of the user by using the biometric information detected by the first sensor 111. The processor 120 may obtain a plurality of pieces of the health state information by using a piece of biometric information. For example, if the biometric information is a bioelectrical impedance of the user, the processor 120 may obtain health state information such as body fat, skin characteristics (for example, body water), strength of muscle, presence of edema, amount of skeletal muscle, amount of muscle, a degree of obesity, body composition percentages, or amount of abdominal visceral fat by using a bioelectrical impedance. Additionally, if the biometric information is a bioelectrical impedance of the user, the processor 120 may obtain health state information such as a highest blood pressure, a lowest blood pressure, elasticity of blood vessels, or presence of heart disease. Blood glucose and cholesterol may be the biometric information as well as the health state information.

If the controller 130 receives a command of displaying the health state information (in a case of YES in operation S430), the controller 160 may control the projector 131 to display the health state information on a part of the user's body. If the user presses a key for display on the user input unit 150, the controller 160 may receive a command of displaying the health state information. Alternatively, movement of the user, for example, movement of the projection surface 310 is not detected, the controller 160 may determine that a command of displaying the health state information is input through the user input unit 150.

The projector 131 may display the health state information on a part of the user's body. In other words, the part of the user's body may be the projection surface 310. For example, the projector 131 may display the health state information on the user's hand. The projector 131 may display the health state information to be in parallel with the reference axis R regardless of a location of a wrist. The processor 120 may determine an angle at which the health state information is to be displayed with respect to the reference axis R, so as to display the health state information to be in parallel with the reference axis R as described above.

Figure 5:
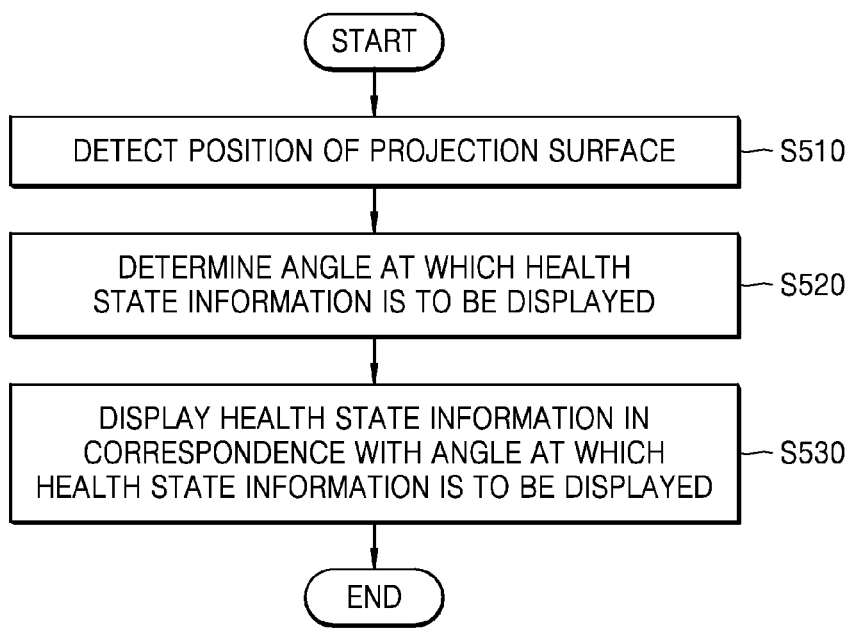
FIG. 5 illustrates a flowchart of a method of displaying health state information, the method being performed by the portable healthcare device, according to an exemplary embodiment.

FIG. 5 illustrates a flowchart of a method of displaying health state information, the method being performed by the portable healthcare device 100, according to an exemplary embodiment.

If a user command of displaying the health state information is received, the second sensor 112 detects a position or an orientation angle of the projection surface 310 in operation S510. For example, the second sensor 112 may detect an angle between the projection axis P and the reference axis R.

In operation S520, the controller 160 may determine an angle at which the health state information is to be displayed, by using the detected angle. The controller 160 may determine an angle, which has a same size as that of the detected angle but is in a reverse direction to the detected angle, as the angle at which the health state information is to be displayed. For example, if the detected angle is 30°, the controller 160 may determine −30° as the angle at which the health state information is to be displayed.

Additionally, the controller 160 may control the projector 131 to rotate an image of the health state information through the angle at which the health state information is to be displayed and display the rotated image of the health state information. When the image of the health state information is rotated through the angle at which the health state information is to be displayed, the displayed health state information becomes in parallel with the reference axis R.

Figure 6:
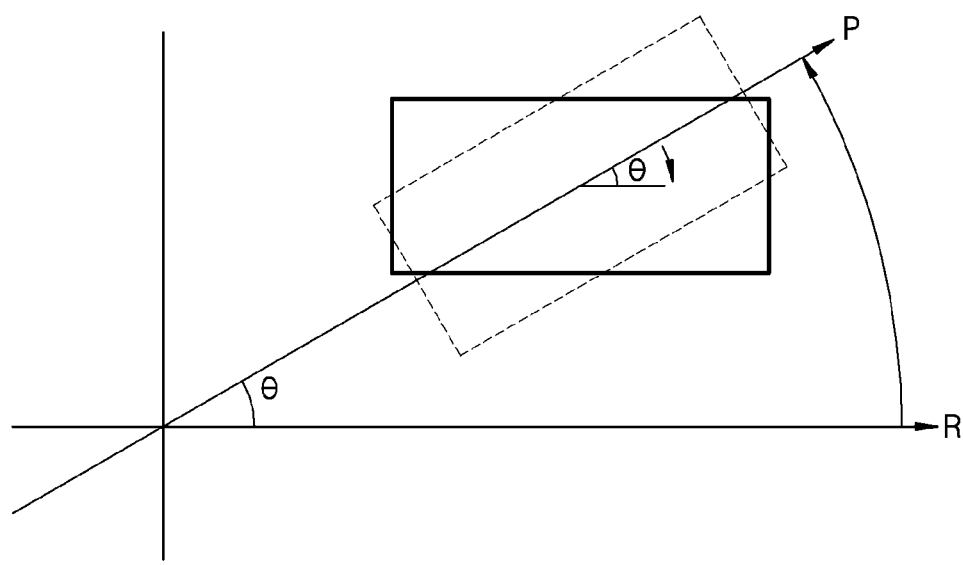
FIG. 6 illustrates a reference diagram for explaining displaying of health state information both before and after rotation, according to an exemplary embodiment.

FIG. 6 illustrates a reference diagram for explaining displaying of health state information both before and after rotation, according to an exemplary embodiment. As shown in FIG. 6, if the health state information is displayed in parallel with the projection axis P when the projection axis P is inclined at an angle of θ degrees (θ°) with respect to the reference axis R, a user may feel uncomfortable when viewing the health state information. This is because a viewpoint of the user is generally in parallel with the reference axis R. Accordingly, according to an exemplary embodiment, the portable healthcare device 100 may rotate the image of the health state information by −θ degrees (−θ°) and display the rotated image of the health state information. Since the rotated health state information is displayed to be in parallel with the reference axis R, visibility of the health state information for the user may be enhanced.

Figure 7A:
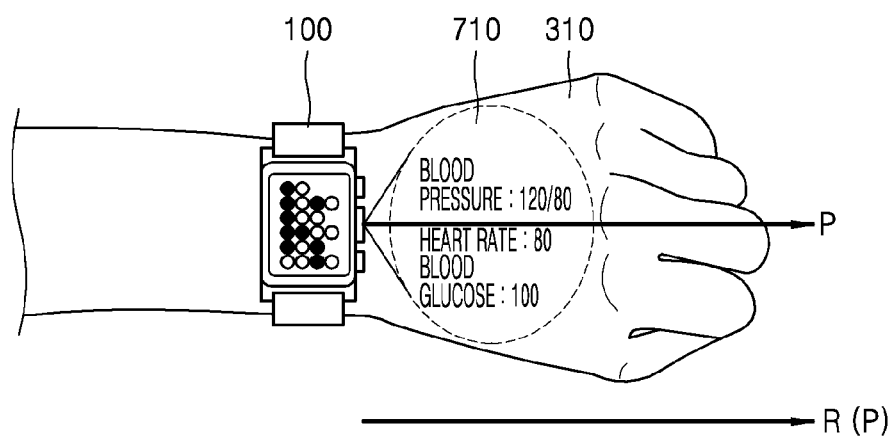
FIGS. 7A through 7C illustrate reference diagrams for explaining health state information along a projection axis, according to an exemplary embodiment.
Figure 7B:
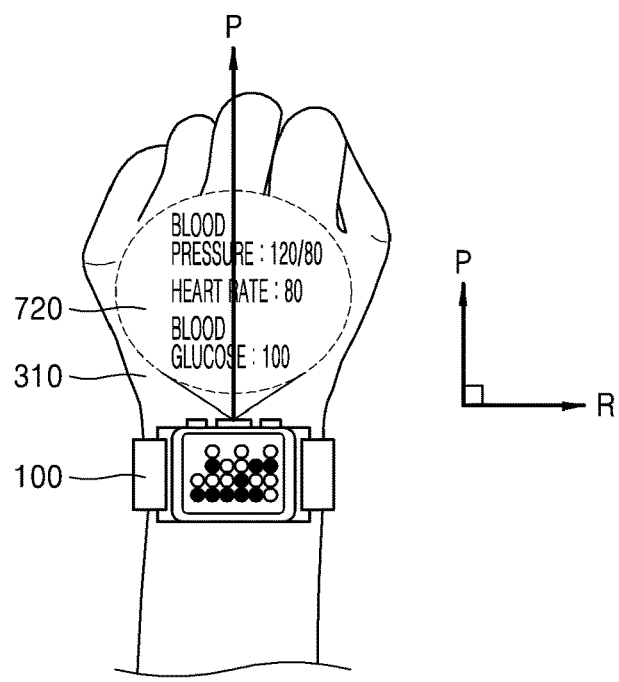
Figure 7C:
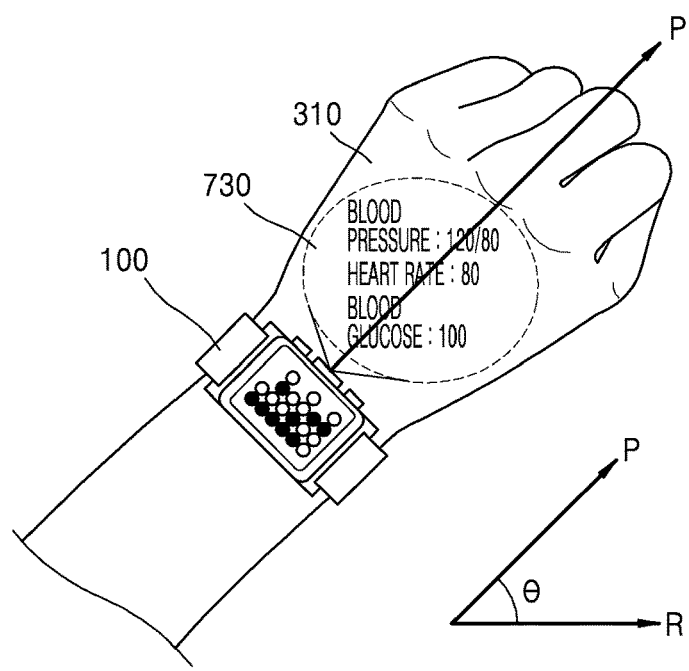

FIGS. 7A through 7C illustrate reference diagrams for explaining health state information 710 along the projection axis P, according to an exemplary embodiment. As shown in FIG. 7A, if the projection axis P is in parallel with the reference axis R, the processor 120 may generate and display an image of the health state information 710 on the projection surface 310 without rotating the image of the health state information 710. Additionally, as shown in FIG. 7B, if it is determined that the projection axis P is inclined at an angle of +90° with respect to the reference axis R according to movement of a user, the controller 160 may determine an angle at which the health state information is to be displayed as −90°, and control the projector 131 to rotate the image of the health state information 720 by −90° and display the rotated image of the health state information. Thus, the projector 131 may display the image of the health state information 720 to be in parallel with the reference axis R. Additionally, as shown in FIG. 7C, if an angle between the projection axis P and the reference axis R is +θ°, the controller 160 may determine an angle at which the health state information is to be displayed as −θ°, and control the projector 131 to rotate the image of the health state information 720 by −θ° and display the rotated health state information. Even if the projection axis P is inclined at +θ° with respect to the reference axis R, the rotated health state information may be displayed in parallel with the reference axis R.

Figure 8:
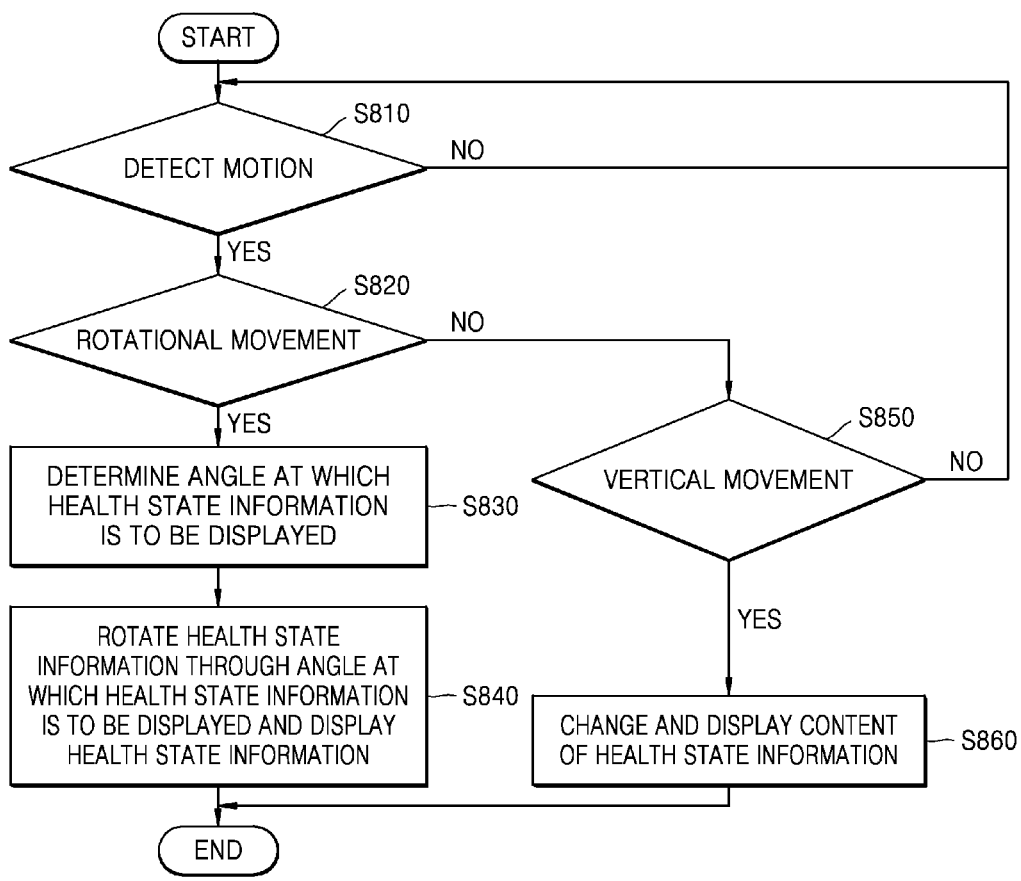
FIG. 8 illustrates a reference diagram for explaining health state information according to movement of a projection axis, according to an exemplary embodiment.

According to an exemplary embodiment, the portable healthcare device 100 may employ various methods of displaying health state information in correspondence with movement of the projection axis P. FIG. 8 illustrates a reference diagram for explaining a method of displaying health state information according to movement of the projection axis P, according to an exemplary embodiment.

In operation S810, the second sensor 112 may detect movement of the projection surface 310. The controller 160 may determine whether or not the detected movement includes rotational movement or linear movement.

If it is determined that the detected movement includes rotational movement (in a case of YES in operation S820), the controller 160 may determine an angle at which the image of health state information is to be displayed in operation S830. The angle at which the health state information is to be displayed may correspond to a rotation angle according to the rotational movement. For example, the angle at which the image of the health state information is to be displayed may have a same absolute value as an absolute value of the rotational angle and may be in a reverse direction to the rotational angle. As such, the controller 150 may determine a position of the portable healthcare device 100 in relation to the user of the portable healthcare device 100. Information of the position of the portable healthcare device 100 may include at least one of an actual location (e.g., global positioning system (GPS) coordinates) of the portable healthcare device 100, an orientation or rotation angle of the portable healthcare device 100, and an orientation or rotation angle of the projection surface 310. According to the present embodiment, the orientation angle of the portable healthcare device 100 may be the same as the orientation angle of the projection surface 310, but the present embodiment is not limited thereto. In that case that the projector 131 is configure to adjust a direction of a beam projected from the projector 131, the orientation angle of the portable healthcare device 100 may be different from the orientation angle of the projection surface 310.

In operation S840, the controller 160 may control the projector 131 to rotate the health state information through the angle at which the health state information is to be displayed and display the rotated health state information. The health state information, which is rotated through the angle at which the health state information is to be displayed and displayed, may be in parallel with the reference axis R. A method of determining an angle at which the health state information is to be displayed according to rotational movement is identical to the method of determining an angle at which the health state information is to be displayed which is described with reference to FIG. 5. However, the method described with reference to FIG. 5 is different from the method described with reference to FIG. 8 in that an angle at which the health state information is to be displayed is determined with reference to the reference axis R in FIG. 5, whereas an angle at which the health state information is to be displayed is determined with reference to the projection axis P before the health state information is rotated in FIG. 8.

If it is determined that the detected movement includes linear movement (in a case of YES in operation S850), the controller 160 may change and display content of the health state information in operation S860. For example, if it is determined that the projection surface has moved toward the user's eyes due to the linear movement, the controller 160 may display detailed information of the displayed health state information. The detailed information of the displayed health state information may include a larger amount of information than the health state information displayed before the linear movement is performed. For example, if health state information is about blood glucose and displayed health state information is about current blood glucose, and if it is determined that the projection surface 310 has moved toward the user's eyes due to the linear movement, the controller 160 may control the project 131 to further display history of blood glucose information which includes past blood glucose information, in addition to the current blood information. Additionally, the detailed information may include a task for the user to do according to a current health state.

If it is determined that the projection surface has moved away from user's eyes due to the linear movement, the controller 160 may display brief information of the displayed health state information. The brief information of the health state information may include a smaller amount of information than the health state information displayed before the linear movement is performed. For example, if the displayed health state information includes information about current blood glucose and a task for the user to do to enhance a health state of the user, and if it is determined that the projection surface 310 has moved away from the user's eyes, the controller 160 may control the projector 131 to stop displaying the task for the user to do and display only the information about the current blood glucose.

Detailed information and brief information of health state information may be defined in various ways. For example, the detailed information of the health state information may include health state information that may be processed by the portable healthcare device 100, and the brief information of the health state information may include a piece of health state information displayed when it is determined that a detected health state of a user is abnormal, from among the health state information provided in the detailed information. In detail, if the portable healthcare device 100 obtains health state information such body fat, skeletal muscle, a visceral fat amount, basal metabolism, a hydration level, TG, LDL, HDL, or a ratio between LDL and HDL by using biometric information about a bioelectrical impedance, detailed information of the health state information may include the health state information described above, and the brief information of the health state information may include a piece of information of a health state displayed when it is determined that a detected health state of a user is abnormal, from among the health state information provided in the detailed information.

In FIG. 8, it is described that movement of a projection surface is classified into rotational movement and linear movement. However, this is just for convenience of description, and the movement of the project surface may include both the rotational movement and the linear movement. If the movement of the project surface includes both the rotational movement and the vertical movement, the portable healthcare device may change both content of health state information and an angle at which the health state information is to be displayed so as to display the health state information.

Additionally, if the portable healthcare device 100 displays health state information via the projector 131, the portable healthcare device 100 may determine a color and brightness of the health-care information adaptively to external light and a skin tone of a user.

Figure 9:
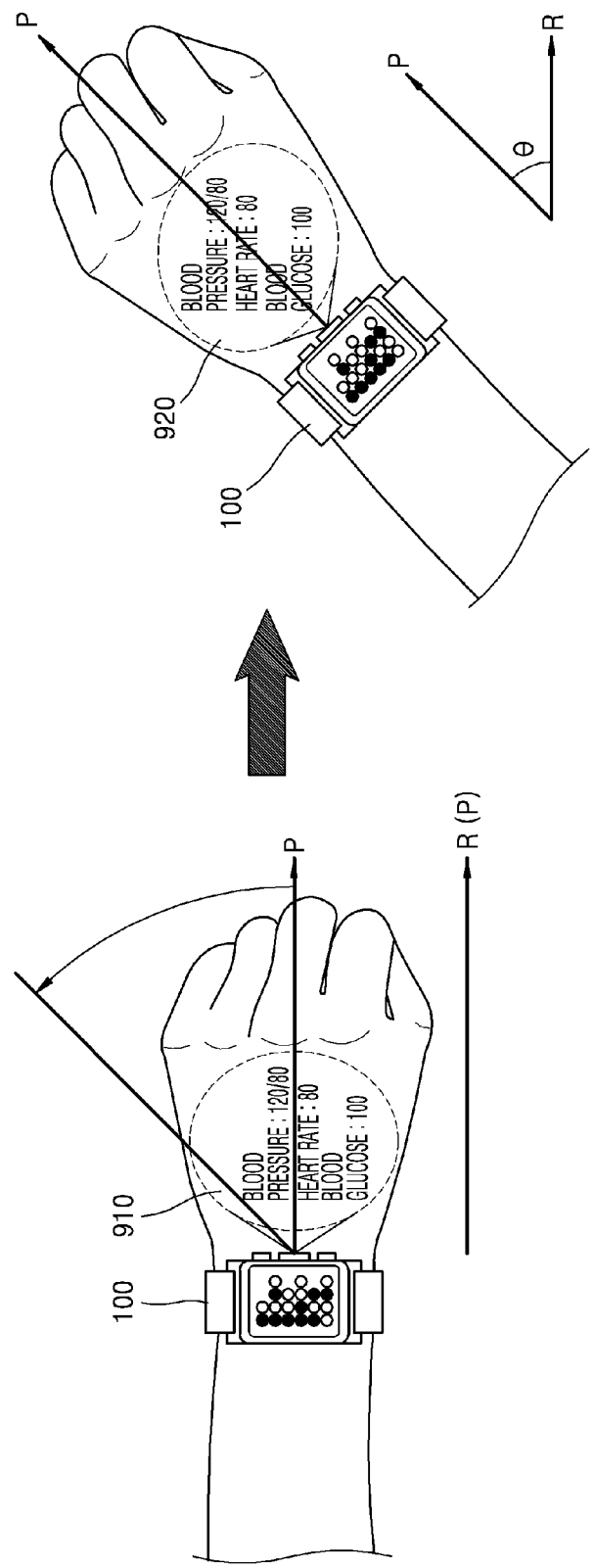
FIG. 9 illustrates a reference diagram for explaining a method of displaying health state information according to movement of a projection surface, according to an exemplary embodiment.

FIG. 9 illustrates a reference diagram for explaining a method of displaying health state information 910 and 920 according to movement of a projection surface, according to an exemplary embodiment. As shown in FIG. 9, the portable healthcare device 100 may display the health state information 910 to be in parallel with the reference axis R. If a user rotates his/her wrist by +θ degrees, the controller 160 determines an angle at which the health state information 910 is to be displayed as an angle of −θ degrees which has a same size as that of the angle of +θ degrees and is in a reverse direction to the angle of +θ degrees. Then, the portable healthcare device 100 rotates the health state information 910 by +θ degrees and displays the rotated health state information 920 as shown in FIG. 9. Since health state information is rotated through an angle in a reverse direction to an angle at which the projection surface is rotated, visibility of the health state information may be maintained.

Figure 10:
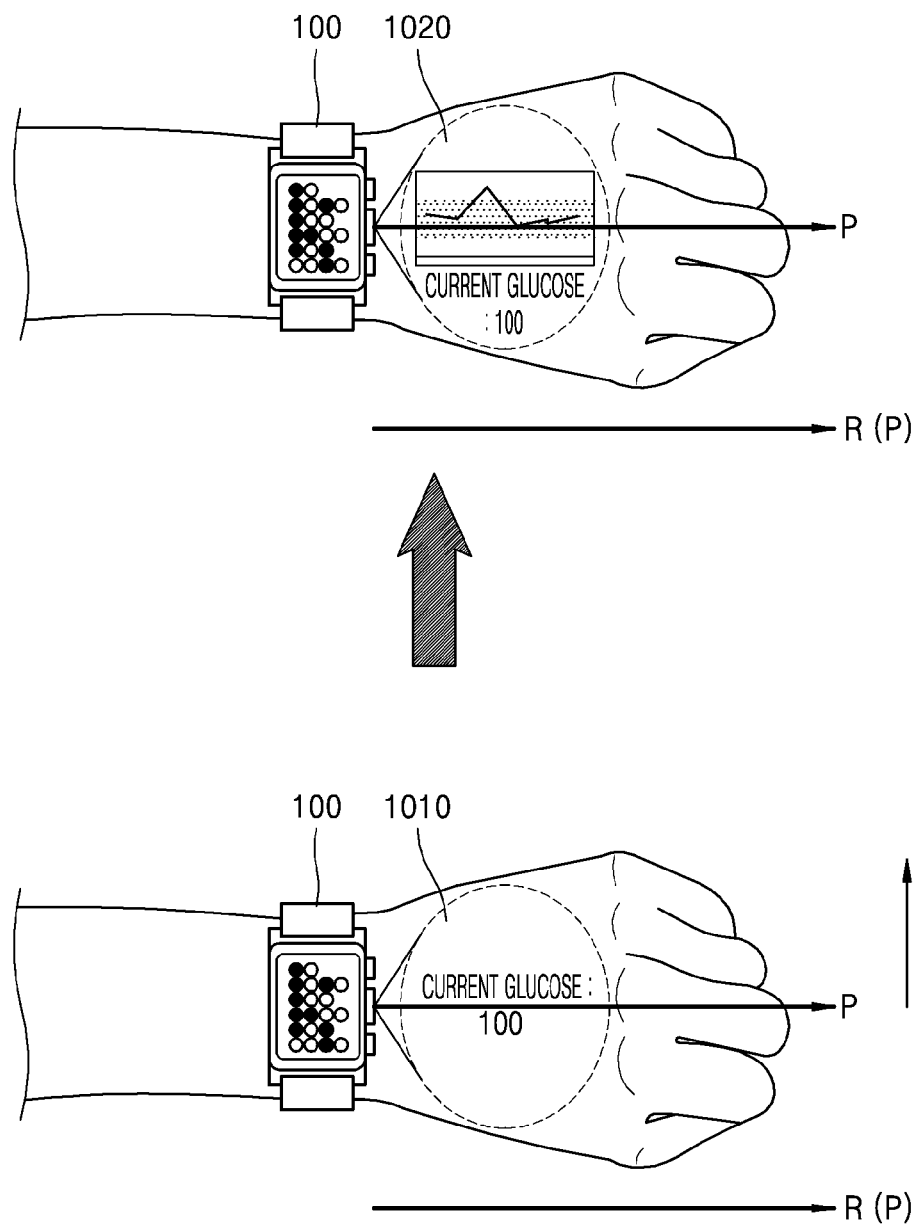
FIG. 10 illustrates a reference diagram for explaining a method of displaying health state information according to linear movement of a projection surface, according to an exemplary embodiment.

FIG. 10 illustrates a reference diagram for explaining a method of displaying health state information 1010 according to linear movement of a projection surface, according to an exemplary embodiment. As shown in FIG. 10, the portable healthcare device 100 may display the health state information 1010 to be in parallel with the reference axis R. For example, the portable healthcare device 100 may display information about current blood glucose as the health state information 1010. If the user moves his/her arm so that a projection surface moves towards the user's eyes, the portable healthcare device 100 may display detailed information such as history of blood glucose and health state information about current blood glucose as the health state information 1020.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A portable healthcare device comprising:
    a first sensor configured to detect biometric information of a user;
    a processor configured to obtain health state information of the user from the biometric information;
    a projector configured to be disposed on a first area of the user and project an image of the health state information along a projection axis and onto a projection surface of a second area of the user, the projection axis being located in a plane obtained by extending the projection surface;
    a second sensor disposed at the projection axis and configured to detect a movement of the projection surface; and
    a controller configured to control the projector to project the image of the health state information in parallel with a reference axis that connects a left side of the user to a right side of the user and is located in the plane, regardless of an orientation angle of the portable healthcare device, the orientation angle being an angle between the projection axis and the reference axis,
    wherein the controller is further configured to, in response to the orientation angle being an acute angle, rotate the image of the health state information by an angle, having a same absolute value as an absolute value of the orientation angle, in a direction reverse to the orientation angle, and control to display the rotated image,
    wherein the controller is further configured to, in response to detecting of a linear movement of the projection surface by the second sensor, display content that is separate from content of the image of the health state information that was displayed prior to the linear movement, and
    wherein the controller is further configured to control to display detailed information of the health state information in response to determining that the projection surface has moved toward eyes of the user to the linear movement.

2. The portable healthcare device of claim 1, wherein the second sensor is configured to detect the orientation angle of the portable healthcare device.

3. The portable healthcare device of claim 1, wherein the first area is a wrist of the user.

4. The portable healthcare device of claim 1, wherein the second area is a hand of the user.

5. The portable healthcare device of claim 1, wherein the detected movement corresponds to a rotational movement of the projection surface, and the controller is further configured to determine the angle at which the health state information is to be displayed in correspondence with the rotational movement.

6. The portable healthcare device of claim 5, wherein the angle at which the health state information is to be displayed has a same absolute value as an absolute value of a rotation angle of the rotational movement and is in a reverse direction to the rotation angle of the rotational movement.

7. The portable healthcare device of claim 1, wherein the controller is further configured to control the projector to display detailed information of the health state information in response to determining that the projection surface has moved toward eyes of the user due to the linear movement.

8. The portable healthcare device of claim 1, wherein the controller is further configured to control the projector to display brief information of the health state information in response to determining that the projection surface has moved away from eyes of the user due to the linear movement.

9. The portable healthcare device of claim 1, wherein the controller is further configured to control the projector to display the image of the health state information in response to determining the projection surface is not being moved based on a result of the detecting performed by the second sensor.

10. A method of operating a portable healthcare device, the method comprising:
 detecting biometric information of a user;
 obtaining health state information of the user from the biometric information;
 projecting, along a projection axis and onto a projection surface of a body of the user, an image of the health state information in parallel with a reference axis, regardless of an orientation angle of the portable healthcare device;
 detecting a movement of the projection surface; and
 in response to detecting of a linear movement of the projection surface, displaying content that is separate from content of the image of the health state information that was displayed prior to the linear movement,
 wherein the projection axis and the reference axis are located in a plane obtained by extending the projection surface, the reference axis connects a left side of the user to a right side of the user, and the orientation angle is an angle between the projection axis and the reference axis,
 wherein the projecting comprises, in response to the orientation angle being an acute angle, rotating the image of the health state information by an angle, having a same absolute value as an absolute value of the orientation angle, in a direction reverse to the orientation angle, and displaying the rotated image, and
 wherein the displaying the content comprises displaying detailed information of the health state information in response to determining that the projection surface has moved toward eyes of the user to the linear movement.

11. The method of claim 10, further comprising:
 detecting an angle between the projection surface and the reference axis; and
 determining the detected angle between the projection surface and the reference axis as the orientation angle.

12. The portable healthcare device of claim 10, wherein the projection surface is a hand of the user.

13. The portable healthcare device of claim 10, wherein the displaying the content further comprises displaying brief information of the health state information in response to determining the projection surface has moved away from eyes of the user due to the linear movement.

* * * * *